United States Patent [19]

Hermelin et al.

[11] Patent Number: 4,973,480

[45] Date of Patent: *Nov. 27, 1990

[54] TAMPER EVIDENT PHARMACEUTICAL CAPSULE

[75] Inventors: Marc S. Hermelin; Mitchell I. Kirschner; George N. Paradissis, all of St. Louis, Mo.

[73] Assignee: K.V. Pharmaceutical Co., St. Louis, Mo.

[21] Appl. No.: 370,875

[22] Filed: Jun. 23, 1989

[*] Notice: The portion of the term of this patent subsequent to Jul. 4, 2006, has been disclaimed.

Related U.S. Application Data

[63] Continuation of Ser. No. 30,465, Mar. 25, 1987, Pat. No. 4,844,906.

[51] Int. Cl.⁵ ............................................. A61K 9/48
[52] U.S. Cl. .................................. 424/454; 424/453; 424/456
[58] Field of Search ........................... 424/454, 453

[56] References Cited

U.S. PATENT DOCUMENTS

| | | | |
|---|---|---|---|
| 4,371,783 | 2/1983 | Grimmel et al. | 250/226 |
| 4,478,658 | 10/1984 | Wittwer | 156/69 |
| 4,677,812 | 7/1987 | Tayebi. | |
| 4,844,906 | 7/1989 | Hermelin et al. | |

OTHER PUBLICATIONS

The Theory and Practice of Industrial Pharmacy, Lachman et al., 1970, pp. 197-225 and 380.
Remmington's Pharmaceutical Sciences, Robinson, 15th edition, 1975, 1608-1617.

Primary Examiner—Merrell C. Cashion, Jr.
Assistant Examiner—Leon R. Horne
Attorney, Agent, or Firm—Sandler, Greenblum & Bernstein

[57] ABSTRACT

A tamper evident pharmaceutical capsule which contains an active agent. The capsule is coated on its external surfaces to provide an indication of tampering.

19 Claims, No Drawings

TAMPER EVIDENT PHARMACEUTICAL CAPSULE

This is a continuation of application Ser. No. 030,465 filed Mar. 25, 1987, now U.S. Pat. No. 4,844,906.

BACKGROUND OF THE INVENTION

I. Field of the Invention

The invention relates to pharmaceutical capsules containing an agent. In particular, the invention is directed to pharmaceutical capsules which are tamper evident.

II. Description of the Prior Art

In recent years the tampering with pharmaceutical capsules has become a nationwide concern and a new form of terrorism. A portion of the pharmaceutical agent is removed and a lethal dosage of poison is substituted. In the alternative, the foreign compound is injected into the capsule by means of a syringe. The unsuspecting victim orally injects the capsule and dies. Catching the perpetrator of the crime is almost impossible.

Many manufacturers at great expense have succumbed to the terrorists and stopped manufacturing products in the capsule form. Thus, depriving the public of a popular form of drug treatment. Other manufacturers have attempted to market their products in tamperproof packaging.

One common method of protecting the capsules is by sealing the packaging cartons and bottles. This method has the obvious disadvantage that the container can be difficult to open. Also, sealing the closure is often an expensive process.

Two other methods involve sealing the capsule joint. These involve placing a gelatin band around the joint or welding the joint. Welding techniques include heat, ultrasonic or the use of a water mixture to form an adhesive seal. None of these methods preclude the tampering of the capsule by injection of a foreign compound by use of a needle.

Coating of tablets is well known in the art. However, such coatings which contain between 2–4% solids are not designed to exhibit tamper evident characteristics since tampering of tablets has not been found to be a problem. Also, capsules have been coated for limited purposes. These coatings decrease the product tackiness, or aid in retaining the product gloss or facilitate the insertion a rectal suppository. None of these coatings produce a capsule with tamper evident qualities.

The present invention is advantageous for a number of reasons. First, it provides a means for the consumer to visually identify tampered capsules. Second, it provides a means of completely sealing a capsule. Thirdly, the method of the invention is very economical and does not diminish or substantially alter the effectiveness of the capsule and agent inside the capsule. Fourth, the invention provides a means of preventing tampering either by separating the capsule into two sections or through injection. And, fifth, the invention permits the use of products developed and/or approved by the FDA for marketing in capsule form to continue to be marketed without a major reformulation or development of a different dosage form.

SUMMARY OF THE INVENTION

A pharmaceutical capsule comprising an agent whose exposed outside surface has been at least 66% covered by a tamper evident coating. The invention also discloses a method of producing a tamper evident pharmaceutical capsule comprising coating at least 66% of the exposed outside surface of a capsule containing an agent with a tamper evident coating.

DESCRIPTION OF THE PREFERRED EMBODIMENTS

Hard gelatin capsules are well known in the pharmaceutical industry. Their sole function is to act as a container for the delivery of a wide variety of agents or medicaments including powders, particles, pellets, and liquids. The agents usually contained in such capsules is well known. May consumers prefer capsules to other drug delivery forms.

Usually, hard gelatin capsules are prepared in two sections by dipping stainless steel pins into a gelatin solution and subsequently drying them. Other methods, such as, extrusion or molding have been used in conjunction with capsules formed from cellulose, cellulose derivatives, natural hydrocoloids and starches. Following formation of the capsule sections they are filled using well known means and fitted together.

It has been found that by applying a coating to at least 66%, preferably 100%, of the external surface area of the capsule a tamper evident capsule is obtained. The coating of the present invention usually contain at least a 6% solids content by weight and preferably over a 10% solids content.

Some of the coating materials, which usually exhibit film forming characteristics, are cellulose and its derivatives. The compounds can be dissolved in an appropriate solvent such as water of methylene chloride or acetone or alcohol(s) or glycols or a number of cosolvent systems.

A variety of other components/modifiers such as colorants, opasifiers, plastisizers surfactants, viscosity builders or powders are being used to enhance various properties of the film.

A typical film forming solutions comprise:

| | |
|---|---|
| Methocel | 10% |
| Methanol | 40% |
| Methylene Chloride | 50% |
| Cellulose Derivatives | 1–30% |
| Polyethylene Glycol (or other glycols) | 1–15% |
| Water | 48–55% |
| Acrylic Resins (Derivatives and copolymers) | 1–15% |
| Talc and/or Magnesium Stereate | 0–5% |
| Alcohol(s) or Methylene Chloride or cosolvents | 99–80% |
| Acrylic Resins (Derivatives and Copolymers) | 5–30% |
| Plastisizers | 0–3% |
| Talc and/or Silica Dioxide | 0–6% |
| Antifoam emulsion | 0.5–1% |
| Water | 94.5–87% |

A preferred method of producing the tamper evident capsules is to place the capsules applying one of the above solutions to the capsules by means of a conventional spraying system. Ambient or hot air can also be used to dry if necessary.

The total amount of solids deposited on the capsule can vary from 1% to 40% by weight depending on the sizes of the capsule and the desirable effect.

The final product (capsule) can be polished by means of applying a clear film forming solution at room temperatures such as the above mentioned one or such as the one below:

| Cellulose or Cellulose derivatives | 3% |
|---|---|
| Ethylcellulose | 1% |
| Methanol | 20% |
| Methylene Chloride | 76% |

Other more traditional means of polishing the final product such as Carnauba wax, glycols, etc. can also be used.

It is also possible to utilize a number of coating compounds or active agents in the coating to achieve a desired effect. For instance, an enteric coating can be applied as a one layer of either a single or multilayer coating or in combination with another coating solution. Also, the coating can be used in conjunction with bands that protect the capsule joint. The uses of multiple layers has been found to provide a preferred coating system for tamper evident applications. Usually the different layers are of different colors which makes the tampering evident to the consumer since the inner coating's coloring becomes visable upon tampering. The first or inner coat comprises a suitable powder(s) such as powder sugar, kaolin, dicalcium phosphate, tricalcium phosphate, calcium carbonate, etc. which is applied on to the capsule with the aid of a solution such as polyvinylpyrrolidone, cellulose derivatives, acacia and other natural or synthetic (hydro) colloids, etc. to form sufficient tamper resistent barrier. The powders when used singly or in combination can contain a variety of other compounds/modifiers such as silica dioxide, starch, etc. to improve certain characteristics such as flow ability, anticaking, dryness, etc.

The capsules after being coated with a first coating are finished by application of a coating using the same process/materials as described previously that is, one or more a film forming solutions such as those containing cellulose or cellulose derivatives. The total amount of solids deposited on the capsule can be up to 50% by weight depending on the size of the capsule and the desirable effect. This method provides a thicker coating layer with better sealing properties and a smoother look.

We claim:

1. A method of producing a tamper evident pharmaceutical capsule comprising coating at least 66% of the exposed outside surface of a capsule containing an agent with a tamper evident coating, wherein the solid content of said coating is 1 to 50% by weight.

2. The method of claim 1, wherein the solid content of said taper evident coating is at least 6% by weight.

3. The method of claim 1, wherein the solid content of said tamper evident coating is at least 10% by weight.

4. The method of claim 1, wherein the solid content of said tamper evident coating is at least 20% by weight.

5. The method of claim 1, wherein said tamper evident coating contains cellulose or cellulose derivatives.

6. The method of claim 1, wherein said capsule includes two sections that are joined together, and the joint of the capsule is sealed with a gelatin band.

7. The method of claim 1, wherein said tamper evident coating comprises multiple layers.

8. The method of claim 1, wherein the coating comprises an active agent.

9. The method of claim 7, wherein one of said multiple layers comprises a powder based coating.

10. The method of claim 7, wherein at least one of said multiple layers is a different color.

11. A tamper evident capsule comprising a capsule whose exposed outside surface has been at least 66% covered by a tamper evident coating, wherein the solid content of said coating is 1 to 50% by weight.

12. The capsule of claim 11, wherein said tamper evident coating includes a solid content of at least 6% by weight.

13. The capsule of claim 11, wherein said tamper evident coating includes a solid content of at least 10% by weight.

14. The capsule of claim 11, wherein said tamper evident coating includes a solid content of at least 20% by weight.

15. The capsule of claim 11, wherein said tamper evident coating contains cellulose or cellulose derivatives.

16. The capsule of claim 11, wherein said capsule includes two sections that are joined together, and the joint of the capsule is sealed with a gelatin band.

17. The capsule of claim 11, wherein said tamper evident coating comprises multiple layers.

18. The capsule of claim 17, wherein at least one of said multiple layers is a different color.

19. The capsule of claim 17, wherein at least one of said multiple layers comprises an active agent.

* * * * *